(12) United States Patent
Feng et al.

(10) Patent No.: US 6,566,588 B1
(45) Date of Patent: *May 20, 2003

(54) PLANTS TRANSFORMED WITH A NUCLEIC ACID ENCODING THE HYPERSENSITIVE RESPONSE ASSOCIATED PROTEIN AMPHIPATHETIC PROTEIN-1

(75) Inventors: Teng-Yung Feng, Taipei (TW); Hao-Jan Lin, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 09/328,553

(22) Filed: Jun. 9, 1999

Related U.S. Application Data

(63) Continuation-in-part of application No. 09/049,577, filed on Mar. 27, 1998, now Pat. No. 5,968,804.

(51) Int. Cl.⁷ .......................... C12N 15/29; C12N 15/82
(52) U.S. Cl. ....................... 800/301; 536/23.6
(58) Field of Search ................................ 800/279, 301; 435/419, 418, 468; 536/23.6

(56) References Cited

U.S. PATENT DOCUMENTS 5,968,804 A * 10/1999 Feng et al. .............. 435/252.3

OTHER PUBLICATIONS

John, I. et al. Accession No. Q43517, Jul. 15, 1998.*
Morel, J. and Dangl, J. L. "Suppressors of the Arabidopsis Isd5 Cell Death Mutation Identify Genes Involved in Regulation Disease Resistance Responses." 1999, Genetics, vol. 151, pp. 305–319.*
Greenberg, J. T. and Ausubel, F. M. "Arabidopsis mutants compromised for the control of cellular damage during pathogenesis and aging." 1993, The Plant Journal, vol. 4, pp. 327–341.*
John, I. et al., "Cloning and characterization of tomato leaf senescence–related cDNAs." 1997, Plant Molecular Biology, vol. 33, pp. 641–651.*
Greenberg, J. T. "Programmed Cell Death in Plant–Pathogen Interactions." 1997, Annu. Rev. Plant Physiol. Plant Mol. Biol., vol. 48, pp. 525–545.*
Ono, E. et al., "Essential role of the small GTPase Rac in disease resistance of rice." 2001, PNAS, vol. 98, pp. 759–764.*
Broekaert et al., "Plant Defensins: Novel Antimicrobial Peptides as Components of the Host Defense System", Plant Physiology 108(4):1353–1358.
Powell et al., "Synthetic Antimicrobial Peptide Design", Mol. Plant–Microbe Interact. 8(5):792–794.
Terras et al., "Small Cysteine–rich Antifungal Proteins from Radish: Their Role in Host Defense", The Plant Cell 7(5):573–588.
Zhong et al., "Design and Synthesis of Amphipathic Antimicrobial Peptides", Int. J. Pept. Protein Res. 45(4):337–347.

* cited by examiner

*Primary Examiner*—Amy J. Nelson
*Assistant Examiner*—Anne Kubelik
(74) *Attorney, Agent, or Firm*—Fish & Richardson P.C.

(57) ABSTRACT

This invention relates to transgenic plants containing an amphipathic protein-1 gene, and isolated nucleic acids encoding an amphipathic protein-1. Expression of the amphipathic protein-1 gene in a transgenic plant decreases a hypersensitive response in the transgenic plant.

6 Claims, No Drawings

SEQUENCE LISTING

```
<160> NUMBER OF SEQ ID NOS:  9

<210> SEQ ID NO 1
<211> LENGTH: 294
<212> TYPE: DNA
<213> ORGANISM: Capsicum annuum
```

-continued

```
<400> SEQUENCE: 1
atggcttcat acaaagtgaa acttatcaca cctgacggac caatagaatt tgattgccca      60
gataatgtgt acattcttga tcaagctgag gaagcaggac atgatcttcc ttattcgtgc     120
agggcaggtt cttgctcatc ttgtgctggt aaaattgctg gtggagctgt tgatcaaact     180
gatggcaact tcttgatga tgaccaatta gaggagggat gggtgctaac ttgtgttgct     240
tatccacagt ctgatgttac tattgagact cacaaagagg cagaactcgt gggc           294

<210> SEQ ID NO 2
<211> LENGTH: 144
<212> TYPE: PRT
<213> ORGANISM: Capsicum annuum

<400> SEQUENCE: 2

Met Ala Ser Val Ser Ala Thr Met Ile Ser Thr Ser Phe Met Pro Arg
 1               5                  10                  15

Lys Pro Ala Val Thr Ser Leu Lys Pro Ile Pro Asn Val Gly Glu Ala
                20                  25                  30

Leu Phe Gly Leu Lys Ser Ala Asn Gly Gly Lys Val Thr Cys Met Ala
            35                  40                  45

Ser Tyr Lys Val Lys Leu Ile Thr Pro Asp Gly Pro Ile Glu Phe Asp
        50                  55                  60

Cys Pro Asp Asn Val Tyr Ile Leu Asp Gln Ala Glu Glu Ala Gly His
    65                  70                  75                  80

Asp Leu Pro Tyr Ser Cys Arg Ala Gly Ser Cys Ser Ser Cys Ala Gly
                85                  90                  95

Lys Ile Ala Gly Gly Ala Val Asp Gln Thr Asp Gly Asn Phe Leu Asp
               100                 105                 110

Asp Asp Gln Leu Glu Glu Gly Trp Val Leu Thr Cys Val Ala Tyr Pro
           115                 120                 125

Gln Ser Asp Val Thr Ile Glu Thr His Lys Glu Ala Glu Leu Val Gly
       130                 135                 140

<210> SEQ ID NO 3
<211> LENGTH: 15
<212> TYPE: PRT
<213> ORGANISM: Gossypium hirsutum

<400> SEQUENCE: 3

Ala Glu Tyr Lys Val Thr Leu Leu Asp Pro Gly Gly Ala Gln Gln
 1               5                  10                  15

<210> SEQ ID NO 4
<211> LENGTH: 15
<212> TYPE: PRT
<213> ORGANISM: Capsicum annuum

<400> SEQUENCE: 4

Ala Thr Tyr Lys Val Lys Leu Val Thr Pro Asp Gly Pro Val Glu
 1               5                  10                  15

<210> SEQ ID NO 5
<211> LENGTH: 15
<212> TYPE: PRT
<213> ORGANISM: Lycopersicum esculentum

<400> SEQUENCE: 5

Ala Thr Tyr Lys Val Lys Leu Ile Thr Pro Glu Gly Pro Phe Phe
 1               5                  10                  15
```

-continued

```
<210> SEQ ID NO 6
<211> LENGTH: 18
<212> TYPE: DNA
<213> ORGANISM: Artificial Sequence
<220> FEATURE:
<223> OTHER INFORMATION: Synthesized degenerate primer
<221> NAME/KEY: variation
<222> LOCATION: (1)...(18)
<223> OTHER INFORMATION: n at positions 3, 6, and 15 is inosine

<400> SEQUENCE: 6
gcnacntaya argtnaar                                            18

<210> SEQ ID NO 7
<211> LENGTH: 14
<212> TYPE: DNA
<213> ORGANISM: Artificial Sequence
<220> FEATURE:
<223> OTHER INFORMATION: Synthesized degenerate primer
<221> NAME/KEY: variation
<222> LOCATION: (1)...(14)
<223> OTHER INFORMATION: n at positions 3, 6, and 12 is inosine

<400> SEQUENCE: 7
acnccngayg gncc                                                14

<210> SEQ ID NO 8
<211> LENGTH: 22
<212> TYPE: DNA
<213> ORGANISM: Artificial Sequence
<220> FEATURE:
<223> OTHER INFORMATION: Synthesized  primer

<400> SEQUENCE: 8
catcttggtc aaagtttgaa tc                                       22

<210> SEQ ID NO 9
<211> LENGTH: 21
<212> TYPE: DNA
<213> ORGANISM: Artificial Sequence
<220> FEATURE:
<223> OTHER INFORMATION: Synthesized  primer

<400> SEQUENCE: 9
aatagaattt gattgcccag a                                        21
```

PLANTS TRANSFORMED WITH A NUCLEIC ACID ENCODING THE HYPERSENSITIVE RESPONSE ASSOCIATED PROTEIN AMPHIPATHETIC PROTEIN-1

CROSS REFERENCE TO RELATED APPLICATIONS

This application is a continuation-in-part of U.S. application Ser. No. 09/049,577, filed Mar. 27, 1998, now U.S. Pat. No. 5,968,804.

BACKGROUND OF THE INVENTION

The hypersensitive response (HR) of higher plants is characterized by the rapid, localized death of plant cells at the site of pathogen invasion. HR occurs during incompatible pathogen/host interactions, such as when a microorganism that normally causes a disease in its host plant infects a non-host plant. The response is associated with resistance against a variety of pathogens, including nematodes, fungi, viruses, and bacteria. For a review of the hypersensitive response, see Dixon et al., Annu Rev Phytopathol 32:479 (1994) and Godiard et al., Curr Opin Genet Dev 4:662 (1994).

The ability of phytopathogenic bacteria to cause HR in resistant or non-host plants is controlled by a cluster of highly conserved bacterial genes named hypersensitive response and pathogenicity (hrp) genes. Most hrp genes are involved in forming a protein secretion apparatus for harpins, heat-stable and proteinaceous proteins which elicit HR when infiltrated into the leaf intercellular spaces of non-host plants. It is known that, when added to a plant cell culture, harpins induce the exchange of $H^+$ and $K^+$ across the plasmalemma to generate active oxygen species (Baker et al., Plant Physiol 102:1341 [1993]).

SUMMARY OF THE INVENTION

This invention relates to amphipathic protein-1 (AP-1) whose presence in a plant decreases the extent or duration of HR in a plant. AP-1 can be introduced to or applied to a plant for the purposes of decreasing HR by direct application of isolated AP-1, transient expression of AP-1 by delivery of a nucleic acid or viral vector into a plant cell, or generation of a transgenic plant expressing a foreign AP-1 gene. A foreign gene or nucleic acid sequence is a gene or sequence that has been introduced into a genome by recombinant genetic techniques.

Accordingly, the invention features a transgenic plant whose genomic DNA includes a foreign nucleic acid encoding a polypeptide. In one aspect, a nucleic acid consisting of the foreign nucleic acid hybridizes under stringent conditions to a nucleic acid consisting of SEQ ID NO:1, the coding sequence for an AP-1 (see below) or its complement. In another aspect, the polypeptide includes an amino acid sequence which is at least 70% (e.g., at least 80, 90, or 95%) conserved with or identical to SEQ ID NO:2.

In addition, the expression of the polypeptide in the transgenic plant decreases a hypersensitive response in the transgenic plant, which can be initiated by a pathogenic bacteria in the transgenic plant. An example of a foreign nucleic acid is one that contains the nucleotide sequence of SEQ ID NO:1.

The invention further includes an isolated nucleic acid encoding a polypeptide having an amino acid sequence at least 70% (e.g., at least 80, 90, or 95%) conserved with or identical to SEQ ID NO:2, the amino acid sequence of an AP-1 (see below). In addition, the invention includes an isolated polypeptide having an amino acid sequence at least 70% (e.g., at least 80, 90, or 95%) conserved with or identical to SEQ ID NO:2. The presence of a polypeptide of the invention, or a polypeptide encoded by a nucleic acid of the invention, in a plant decrease a hypersensitive response in the plant.

A "foreign nucleic acid" in the context of a genome is any nucleic acid whose sequence is not naturally found in that genome. For example, foreign nucleic acids can be inserted into genomes by means of recombinant DNA technology.

A "nucleic acid" encompasses both RNA and DNA, including cDNA, genomic DNA, and synthetic (e.g., chemically synthesized or modified) DNA. The nucleic acid may be double-stranded or single-stranded. Where single stranded, the nucleic acid may be a sense strand or an antisense strand. An "isolated nucleic acid" refers to a nucleic acid which may be flanked by non-natural sequences, such as those of a plasmid or virus. Thus, the nucleic acid can include none, some, or all of the 5' non-coding (e.g., promoter) sequences which are immediately contiguous to the coding sequence. The term, therefore, includes, for example, a recombinant DNA which is incorporated into a vector including an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. The term also includes a recombinant DNA or RNA which is part of a hybrid gene encoding an additional polypeptide sequence. Moreover, the term is meant to include nucleic acid fragments which are not naturally occurring as fragments and would not be found in the natural state.

By "hybridizes under stringent conditions" is meant specific and non-covalent binding to an immobilized reference nucleic acids in the presence of 0.2×SSC (1.75 g/l NaCl, 0.88 g/l $Na_3$citrate·$2H_2O$; pH 7.0) and 0.1% (w/v) sodium dodecylsulfate at 68° C.

The term "isolated" as used herein in reference to a given polypeptide means that the polypeptide is substantially free from other compounds, such as those in cellular material, viral material, or culture medium, with which the polypeptide may have been associated (e.g., in the course of production by recombinant DNA techniques or before purification from a natural biological source). Polypeptides are substantially free from other compounds when they are within preparations that are at least 60% by weight (dry weight) the compound of interest. Preferably, the preparation is at least 75%, more preferably at least 90%, and most preferably at least 99%, by weight the compound of interest. Purity can be measured by any appropriate standard method, for example, by column chromatography, polyacrylamide gel electrophoresis, or HPLC analysis.

Where a particular polypeptide or nucleic acid molecule is said to have a specific percent identity or conservation to a reference polypeptide or nucleic acid molecule the percent identity or conservation is determined by the algorithm of Myers and Miller, CABIOS (1989) which is embodied in the ALIGN program (version 2.0), or its equivalent, using a gap length penalty of 12 and a gap penalty of 4 where such parameters are required. All other parameters are set to their default positions. Access to ALIGN is readily available. See, e g., www2.igh.cnrs.fr/bin/align-guess.cgi on the Internet.

The isolation and characterization of an AP-1 gene of the invention will allow the production of variant forms of AP-1 polypeptides which may have advantageous activities such as greater HR-blocking activity or greater protein stability.

Other features or advantages of the present invention will be apparent from the following detailed description, and also from the claims.

DETAILED DESCRIPTION OF THE INVENTION

The invention relates to amphipathic protein-1, a polypeptide which decreases the extent or duration of HR in plants, e.g., in response to a harpin secreted from a bacterium.

Contemplated within the scope of this invention are recombinant nucleic acids or viruses which allow production of AP-1 in a transformed cell or transgenic organism or allow ease of producing specific or non-specific mutations within the AP-1 reading frame. These recombinant nucleic acids or viruses may further include any one of a variety of sequences upstream of the AP-1 coding sequences, such as strong constitutive promoters; within the AP-1 coding sequence, such as introns containing cis-elements that allow high level expression; or downstream of the AP-1 coding sequence, such as efficient polyadenylation signals. The invention further includes any cells containing or producing such nucleic acids or viruses, and any AP-1 polypeptides produced from such cells.

Also included in the invention are transgenic plants which express or overexpress an AP-1 polypeptide. These plants can be resistant to bacteria-induced HR, as shown in the examples below.

Without further elaboration, it is believed that one skilled in the art can, based on the above disclosure, the isolation of AP-1 polypeptides and genes described below, and the production of HR-resistant transgenic plants expressing AP-1 as shown below, utilize the present invention to its fullest extent. The following examples are to be construed as merely illustrative of how one skilled in the art can isolate and use AP-1 genes and polypeptides from biological sources, and are not limitative of the remainder of the disclosure in any way. Any publications cited in this disclosure are hereby incorporated by reference.

EXAMPLE 1

Isolation of Amphipathic Protein-1

Three plants were used for the extraction of AP-1. Cotton cultivar (*Gossypium hirsutum* L.) was obtained from the Jiangsu Academy of Agricultural Sciences (Nanking, China). Tomato cultivar (*Lycopersicum esculentum*, Moneymaker, CF4) was obtained from Dr. P .J .G. M. De Wit at Agricultural University, Wageningen, The Netherlands and is available as ATCC Nos. 54003 and 54004. Sweet pepper cultivar (*Capsicum annuum*, ECW) was obtained from Dr. C-F. Wang in the Asian Vegetable Research and Developmental Center (AVRDC; Tainan, Taiwan, Republic of China) and is available as AVRDC Accession No. C00165-1.

Healthy leaves from each plant were homogenized in 0.5 M Tris buffer (pH 8.0) in the presence of 1% (w/v) polyvinylpyrrolidone and 1.5% (v/v) n-octanol. The homogenates were filtrated by nylon mesh and centrifuged at 10,000 g for 30 minutes at 4° C. The fatty layer at the top of the centrifuge tubes was collected, resuspended in Tris buffer (0.05 M, pH 7.5) containing 1 mM phenylmethylsulfonylfluoride and gently shaken for at least 1 hour. The amphipathic extracts were obtained from the soluble phase after centrifugation at 10,000 g for 30 minutes at 4° C.

Amphipathic extracts from the three plants were first separated by Sephacryl S-100 gel filtration (Pharmacia Co.) as follows. 6 mg of total protein in a volume of 5 ml were loaded in a 1.5×100 cm column (Bio-Rad) and eluted with Tris buffer (50 mM, pH 7.5) at a flow rate of 0.1 ml/min using the Econo Chromatography system (Bio-Rad). All fractions were tested for their ability to interfere with HR elicitor activity by infiltrating equal amounts of the eluted proteins and harpin$_{Pss}$ into tobacco plant leaves (procedure described below). Fractions 49–51 from all plant sources contained significant HR inhibitory activity. Such fractions were pooled for the next step of purification.

A 1.5×30 cm column (Bio-Rad) containing DEAE Sepharose CL-6B (Pharmacia) was used for further purification. A 0 to 1.0 M NaCl gradient in Tris buffer (50 mM, pH 7.5) was used to elute proteins at a flow rate of 0.5 ml/min, using the Econo Chromatography System. The eluents were desalted using a Microconcentrator with 10 kDa molecular weight cut-off membrane (Amicon Co.) and washed three times with phosphate buffer. Fractions 26–32 from all plant sources showed significant HR inhibitory activity, which correlated with a single 22 kDa polypeptide as visualized by subjecting the various fractions to sodium dodecylsulfate-polyacrylamide gel electrophoresis (SDS-PAGE) and subsequent silver staining. The 22 kDa protein purified as described above is named amphipathic protein-1 or AP-1.

The AP-1 yield from tomato leaves was about $10^{-8}$ gram protein/gram leaf. The yield from sweet pepper or cotton was about $10^{-9}$ gram protein/gram leaf.

The N-terminal amino acids of AP-1 from the three plants were determined. AP-1 was isolated, separated by SDS-PAGE, transferred onto PVDF membranes, and analyzed using a ABI 476A protein sequencer (Applied biosystems, Inc.) as instructed by the manufacturer. The first 15 amino acids of each AP-1 from the three plants were determined as follows:

```
Cotton:   Ala Glu Tyr Lys Val Thr Leu Leu Asp Pro Gly Gly
          Ala Gln Gln (SEQ ID NO:3)

Pepper:   Ala Thr Tyr Lys Val Lys Leu Val Thr Pro Asp Gly
          Pro Val Glu (SEQ ID NO:4)

Tomato:   Ala Thr Tyr Lys Val Lys Leu Ile Thr Pro Glu Gly
          Pro Phe Phe (SEQ ID NO:5)
```

EXAMPLE 2

AP-1 Delays Harpin-Induced Hypersensitive Response

To test the effect of AP-1 on Harpin induced HR, Harpin$_{Pss}$ (harpin from *Pseudomonas syringae* pv. syringae) protein was first prepared. Harpin$_{Pss}$ protein was extracted by the methods described in He et al., Cell 73:1255 (1993). *E. coli* DH5α (pSYH10) containing the harpin$_{Pss}$ gene was grown in Lauria Broth containing ampicillin (50 μg/ml) at 37° C. in the dark and shaken overnight in the presence of isopropyl-β-D-thiogalactoside (IPTG). To obtain harpin$_{Pss}$, the bacteria were washed, sonicated for 30 seconds, and boiled for 10 minutes. After boiling, the extracts were centrifuged at 10,000 g for 10 minutes. Supernatants were desalted by Microconcentrators (Amicon) and were stored at 4° C.

The HR assay was performed as described in Huang et al., J Bacteriol 170:4748 (1988). Fully expanded tobacco leaves (*Nicotiana tabacum* L. cv. Xanthi, available as ATCC Nos. 54037 and 54039) were wounded with a 25 gauge needle to form tiny holes on the lower surfaces of the leaves. Harpin$_{Pss}$ or bacterial cells was infiltrated by pressing a 1 ml blunt syringe through the hole. The infiltrated plant was incubated in a 28° C., 12 hour light/12 hour dark incubator. The HR was recorded by photography.

Various amounts of purified AP-1 were mixed with 10 μg of harpin$_{Pss}$, and the resulting mixture was infiltrated into the intercellular spaces of tobacco leaves. The area of necrosis 20 hours after infiltration in the presence of as little as 50 ng of tomato AP-1 was reduced in comparison with the absence of AP-1.

AP-1 also caused a significant postponement of HR-like necrosis induced by harpin$_{Pss}$-harboring bacteria. Bacteria was infiltrated in the absence or presence of 500 ng of tomato AP-1 into the intercellular spaces of the tobacco leaf at the equivalent of $5 \times 10^6$ CFU/ml. At six days post-inoculation, the bacteria caused significant necrosis in the absence of AP-1. In the presence of AP-1, the infiltrated plant tissue was relatively healthy.

The HR reduction rate was approximately proportional to the dosage of AP-1 in the range from 50 ng to 500 ng and approached 80% reduction of HR at the highest dose at 20 hours post-inoculation. 250 ng of AP-1, which corresponds to a harpin$_{Pss}$ to AP-1 molar ration of 40 to 1, established about a 50% reduction of the HR-necrosis area.

A time-course of AP-1 infiltration was performed with respect to *P. syringae* inoculation. HR was not delayed when AP-1 was infiltrated 30 or 60 minutes prior to inoculation. In contrast, AP-1 delayed HR significantly when AP-1 and bacteria were infiltrated simultaneously.

EXAMPLE 3

AP-1 Suppresses Bacterial Growth

*P. syringae* pv. syringae was infiltrated, along with tomato AP-1, into the intercellular spaces of tobacco leaves. The bacteria population was monitored as described in Li et al., J Bacteriol 174:1742 (1992). $1 \times 10^7$ cfu/ml of log-phase growth bacteria was used for each inoculation. Leaf disks (0.5 cm diameter) punched around the infiltration holes were homogenized in 100 μl phosphate buffer (0.01 M, pH 6.5) and diluted up to 10,000 fold. 100 μl of bacteria were plated on 9 cm LB agar plates, and the colonies counted after overnight growth. Each dilution was plated in triplicate.

Within 48 hours post-inoculation, the population of the bacteria and the bacteria treated with 1 μg of bovine serum albumin (BSA) steadily increased from $10^5$ CFU/ml to $10^7$ CFU/ml per leaf disk. However, in the presence of 1 μg of AP-1, the bacterial population was reduced from an initial $5 \times 10^5$ CFU/ml to $5 \times 10^4$ CFU/ml 16 hours post-inoculation.

EXAMPLE 4

Cloning of an AP-1 cDNA

Total RNA was isolated from pepper leaves (*Capsicum annuum*) as described in Nelson, "Preparation of DNA and RNA from leaves: expanded blades and separated bundle sheath and mesophyll cells" In The Maize Handbook, Freeling et al. editors, pp. 541–545, Springer-Verlag, N.Y., 1994. Two grams of pepper leaves were homogenized, using a Pro 200 homogenizer, in 10 ml of extraction buffer (0.1 M TRIS-HCl, pH 8.5, 0.1 M NaCl, 20 mM EDTA, and 1% lauroyl sarcosine). RNA was separated from DNA by precipitation with 2 M LiCl. First-strand cDNA synthesized using an oligo (dT) primer and Superscript Reverse Transcriptase (GibcoBRL/Life) according to the manufacturer's instructions.

For PCR, 2 μl of RT mixture was combined with 0.6 μM of modified degenerate primer (5'-GCiACiTAYAARGTiAAR-3'; [SEQ ID NO:6]), 0.2 μM of 5'-(dT)N anchor primer, 1 mM dNTP, and 2.5 units of Taq DNA polymerase (GibcoBRL/Life). The sequence of PCR primers used to clone AP-1 were derived from the N-terminal amino acid sequence as described in Example 1 above. The amplification cycle parameters were as follows: 5 minutes at 94° C.; two cycles of 1 minute at 94° C., 2 minutes at 45° C., 1.5 minutes at 72° C.; 38 cycles of 45 seconds at 94° C., 2 minutes at 63° C., 1 minute at 72° C.; and 10 minutes at 72° C. PCR products were purified using a spin-column with a silica-gel binding membrane (Qiagen).

The second, nested PCR was amplified by mixing together 1 μl of the above purified PCR products, 0.4 μM of modified degenerate primer (5'-ACiCCiGAYGGiCC-3'; SEQ ID NO:7), 0.4 μM of 3' oligo 5' (dT)$_{18}$N anchor primer and otherwise treated as indicated immediately above.

RT-PCR products were run on an agarose gel and eluted using a Qiaquick gel extraction kit (Qiagen). The purified cDNA fragments were treated with polynucleotide kinase and ligated into the pT7Blue blunt-end vector (Novagen) according to manufacturer's instructions.

The sequence of cDNA inserts was determined by the dideoxy chain termination method using a Sequenase kit (PE-ABI) and an ABI nucleic acid sequencer.

To amplify the 5' Cap region of the gene, first-strand cDNA was synthesized by performing RT-PCR (GibcoBRL/Life) in the presence of 0.5 μM Capswitch primer (Clontech) and 800 ng pepper mRNA. mRNA was isolated from total pepper RNA using oligo (dT) affinity magnetic particles (Straight-A mRNA Isolation System, Novagen). PCR amplification of the 5' cap region was performed in a 30 μl volume containing 2 μl single-strand cDNA, the 5' Capswitch primer, and 3'-specific primer (5'-CATCTTGGTCAAAGTTTGAATC-3'; SEQ ID NO:8) corresponding to the 3' noncoding region of the AP-1 clone. Amplification was performed using the following parameters: 35 cycles of 94° C. for 45 seconds, 53° C. for 1 minute, and 72° C. for 1 minute; and 5 minutes at 72° C. Following PCR amplification, the Klenow cDNA fragments were purified, treated with polynucleotide kinase, and ligated into pT7Blue Blunt vector (Novagen).

A 785 base pair full-length cDNA clone (pap-1), containing N-terminal deduced amino acid sequences of the putative mature peptide, was isolated. This clone encodes a polypeptide with the same N-terminal amino acids as described in Example 1 above. The pap-1 cDNA clone contains an open reading frame (ORF) of 432 bp, encoding a protein of 144 amino acids, which includes a 47 amino acid putative secretion peptide. The coding sequence of the open reading frame is shown below.

ATGGCTTCATACAAAGTGAAACTTATCACACCTGACGGACCAATAGAATTTGATTGCCCA

GATAATGTGTACATTCTTGATCAAGCTGAGGAAGCAGGACATGATCTTCCTTATTCGTGC

AGGGCAGGTTCTTGCTCATCTTGTGCTGGTAAAATTGCTGGTGGAGCTGTTGATCAAACT

GATGGCAACTTTCTTGATGATGACCAATTAGAGGAGGGATGGGTGCTAACTTGTGTTGCT

TATCCACAGTCTGATGTTACTATTGAGACTCACAAAGAGGCAGAACTCGTGGGC (SEQ ID NO:1)

The deduced amino acid sequence contains a 2Fe-2S domain, a myristoylation site, and two phosphorylation sites. The AP-1 amino acid sequence is shown below.

Met Ala Ser Val Ser Ala Thr Met Ile Ser Thr Ser Phe Met Pro

Arg Lys Pro Ala Val Thr Ser Leu Lys Pro Ile Pro Asn Val Gly

Glu Ala Leu Phe Gly Leu Lys Ser Ala Asn Gly Gly Lys Val Thr

Cys Met Ala Ser Tyr Lys Val Lys Leu Ile Thr Pro Asp Gly Pro

Ile Glu Phe Asp Cys Pro Asp Asn Val Tyr Ile Leu Asp Gln Ala

Glu Glu Ala Gly His Asp Leu Pro Tyr Ser Cys Arg Ala Gly Ser

Cys Ser Ser Cys Ala Gly Lys Ile Ala Gly Gly Ala Val Asp Gln

Thr Asp Gly Asn Phe Leu Asp Asp Asp Gln Leu Glu Glu Gly Trp

Val Leu Thr Cys Val Ala Tyr Pro Gln Ser Asp Val Thr Ile Glu

Thr His Lys Glu Ala Glu Leu Val Gly (SEQ ID NO:2)

To test for the distribution of ap-1 in various plants, genomic DNA was isolated from pepper, tomato, tobacco, cotton, *Arabidopsis thaliana* and Petunia sp. according to Nelson, Id. For PCR detection of ap-1 sequences, a 5' primer in the ap-1 coding sequence (5'-AATAGAATTTGATTGCCCAGA-3'; SEQ ID NO:9) and 3' primer (5'-CATCTTGGTCAAAGTTTGAATC-3'; SEQ ID NO:8) in the 3' untranslated region were used. The 5' primer and the 3' primer was expected to produce a 373 bp PCR product. The PCR was performed in MgCl$_2$ buffer containing 1 mM dNTP, 2.5 units of Taq DNA polymerase, 200 ng genomic DNA and 5% dimethylsulfoxide. The amplification parameters were as follows: 5 minutes at 94° C.; 5 cycles of 1 minute at 94° C., 1 minute at 51° C., and 1 minute at 72° C.; and 30 cycles of 45 seconds at 94° C., 1 minute at 51° C., and 1 minute at 72° C.; and 5 minutes at 72° C.

A 373 bp fragment could be amplified from pepper, tomato, tobacco, Petunia, and cotton genomic DNA but not from Arabidopsis genomic DNA.

EXAMPLE 5

In Vitro Expression of Cloned AP-1

In order to transiently express pepper AP-1 in vivo, the pap1 coding region was subcloned into a bamboo mosaic potexvirus satellite (satBaMV) vector, which is described in Lin et al., Proc Natl Acad Sci USA 93:3138 (1996), hereby designated BSAP1. BASP1 was used to in vitro transcribe an RNA containing the 432 bp ap-1 open reading frame and about 400 bp of viral sequence. The BaMV-L and satBaMV vector transcripts were inoculated, along with the ap-1 transcript, into the tobacco *Nicotiana benthamiana*. Northern blot hybridization was used to detect the replication of viral RNA in tobacco. The total RNA extracted 7 days after inoculation was separated on 1% agarose gels, transferred to nylon membranes, and hybridized with a probe specific to the 3' end of satBaMV (+)RNA as described in Lin et al., (1996) Id. The Northern indicated that the BSAP1 RNA was expressed in the tobacco.

For in vitro translation, the satBaMV vector transcripts were translated in rabbit reticulocyte lysate (Promega) in the presence of $^{35}$S-labeled methionine and analyzed by SDS-PAGE. The in vitro translation produced a 27 kDa protein. The size of the translated protein was about two folds larger than the predicted molecular weight of the ap1 encoded polypeptide (14 kDa), including the putative secretion peptide region.

For expression of AP-1 in *E. coli*, the mature polypeptide of the pap1 clone was cloned into the Bam HI and Hind III sites of the pQE-30 vector (Qiagen) and transformed into the bacterial host strain M15. The N-terminal 6× His-tagged proteins were induced with IPTG and purified by Ni-NTA resin Spin Kits (Qiagen). For immunoblot detection of the 6× His-tagged AP-1 polypeptides, the *E. coli* lysate was run on SDS-PAGE gels, transferred onto nitrocellulose membranes, and detected with $^{RGS}$. His antibodies (Qiagen).

In the above system, the translated protein, which does not include the secretion peptide, was also observed to be double the size (22 kDa) of the predicted molecular weight of AP-1. This size, however, is consistent with the estimated molecular weight of the plant AP-1 polypeptide as described in Example 1 above.

EXAMPLE 6

Cloned AP-1 Delays Harpin$_{Pss}$-Mediated HR

To determine the biological activity of cloned AP-1, a mixture of the purified harpin$_{Pss}$ and *E. coli* expressed pepper AP-1, as obtained in Example 5 above, was infiltrated into tobacco leaves as described in Example 2 above. A light yellowing response was induced by harpin$_{Pss}$ within one day post-inoculation and was followed by the formation of harpin$_{Pss}$-induced necrosis two days post-inoculation. The necrosis area was reduced more than 50% two days post-inoculation when 200 ng AP-1 was co-inoculated with the harpin.

EXAMPLE 7

Cloned AP-1 Suppresses HR Induced by *Erwinia Carotovora* Subsp. Carotovora

Fifty microliters containing different concentrations of the pathogenic bacteria *Erwinia carotovora* subsp. carotovora in the presence or absence of 0.15 $\mu$M AP-1 were inoculated into tobacco leaves and assayed for HR inhibition as described in Example 2 above. *E. carotovora* subsp. carotovora can be obtained as ATCC No. 12312.

AP-1 protected the plant tissue from *E. carotovora*—induced HR necrosis at one day post-inoculation for bacterial concentrations up to $10^7$ CFU/ml.

EXAMPLE 8

Agrobacterium-Mediated Overexpression of AP-1 Suppresses HR Induced by *Xanthomonas campestris* pv. Vesicatoria Agrobacterium-mediated transient overexpression of sweep pepper AP-1 was established in sweet pepper plants as described in Van den Ackerveken et al., Cell 87:1307 (1996). Agrobacterium bacteria was infiltrated into fully expanded leaves of the sweet pepper overexpressing AP-1. Plants were kept for two days at 20° C., 16 hour light/8 hour dark, 100% humidity and then moved to 28° C., 16 hour light/8 hour dark, 80% humidity. Fifty microliters of *Xanthomonas campestris* pv. vesicatoria suspension at $1\times10^4$ CFU/ml was inoculated eight days after the Agrobacterium inoculation in the same region and incubated for 24 hours. *X. campestris* pv. vesicatoria can be obtained as ATCC Nos. 11551 and 11633.

The Agrobacterium-mediated expression of AP-1 prevented HR necrosis induced by the pathogenic *X. campestris.*

EXAMPLE 9

Production of Transgenic Plants Expressing AP-1 and Exhibiting Resistance to HR

The pepper AP-1 gene was cloned into vector pBI121 (Clontech) to form pBISPAP-1. This plasmid drove expression of AP-1 from a CaMV 35S promoter. pBISPAP-1 was introduced into *Agrobacterium tumefaciens* C58C1 cells. Transformed cells were used to infect sterilized tobacco leaf discs, which were then screened for successful transformants on selective MS medium (Gibco BRL) containing kanamycin. The plant transformation procedure used in this Example is further described in McCormick et al., Plant Cell Reports 5:81–84 (1986).

Transformed plant tissue was grown into calli and subsequently into shoots and roots in two to three months under selection pressure. The selected (R0) plants were removed from the selection medium to regular growing conditions in a greenhouse. R0 transgenic tobacco plants were confirmed by performing PCR on R0 plant tissues using a CaMV 35S primer and an ap-1 specific primer.

The screening identified 47 R0 transgenic plants, which were self-pollinated and seeded to produce R1 plants. After one to two months, 17 R1 tobacco lines were obtained. One line, line 76, was further studied.

$10^6$ or $10^7$ CFU/ml of *Erwinia carotovora* pv. carotovora (causative agent of soft rot disease) were separately infiltrated into the leaves of a wild type tobacco plant and of plant clones 76-6 and 76-5. Necrotic regions could be observed on wild type leaves at the site of inoculation at both challenge concentrations. In contrast, 76-6 and 76-5 plant leaves were resistant to challenge at $10^6$ CFU/ml, and the necrosis was reduced in both transgenic plants relative to the wild type plant at the $10^7$ CFU/ml challenge. In addition, the titer of bacteria recovered from the lesions in transgenic plants was significantly reduced in comparison to the titer of bacteria recovered from the lesions induced in the wild type plant.

Two other plants from the same transgenic line, 76-1 and 76-3, were challenged with *Pseudomonas syringae* pv. syringae (causative agent of bacterial fire blight disease) at $10^5$ CFU/ml. At five days post-challenge, 76-1 exhibited no symptoms, while 76-3 exhibited a dried-out HR-like lesion, which was visible as early as 24 hours post-challenge. A HR lesion was visible on the wild type plant.

At 13 days post-challenge, a typical fire blight lesion with its distinctive yellow halo could be observed on the wild type plant. The halo around the lesions on the 76-1 and 76-3 plants were substantially smaller in comparison to the lesions on the wild type plant.

The results in this Example clearly indicate that transgenic plants expressing AP-1 can resist HR disease.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of this invention.

What is claimed is:

1. A transgenic plant whose genomic DNA comprises a foreign nucleic acid encoding a polypeptide, wherein the polypeptide comprises an amino acid sequence which is at least 95% identical to SEQ ID NO:2, and expression of the polypeptide in the transgenic plant decreases a hypersensitive response in the transgenic plant.

2. The transgenic plant of claim 1, wherein the hypersensitive response is initiated by a pathogenic Gram-negative bacterium in the transgenic plant.

3. A transgenic plant whose genomic DNA comprises a foreign nucleic acid comprising SEQ ID NO:1.

4. An isolated nucleic acid encoding a polypeptide comprising an amino acid sequence at least 95% identical to SEQ ID NO:2, wherein the presence of the polypeptide in a plant decreases a hypersensitive response in the plant.

5. The nucleic acid of claim 4, wherein the amino acid sequence is SEQ ID NO:2.

6. The nucleic acid of claim 5, wherein the nucleic acid comprises SEQ ID NO:1.

* * * * *